United States Patent [19]

Driscoll et al.

[11] Patent Number: 4,882,346

[45] Date of Patent: Nov. 21, 1989

[54] CHEMICAL DIFFERENTIATING AGENTS

[75] Inventors: John S. Driscoll, Rockville; Alberto Haces, Frederick; Theodore Breitman, Rockville, all of Md.

[73] Assignee: The United States of America as represented by the Department of Health and Human Services, Washington, D.C.

[21] Appl. No.: 62,422

[22] Filed: Jun. 16, 1987

[51] Int. Cl.$^4$ ........................................... A61K 31/415
[52] U.S. Cl. ................................. 514/389; 548/310; 546/88; 564/153; 564/152
[58] Field of Search ...................... 548/310; 514/389

[56] References Cited

U.S. PATENT DOCUMENTS 3,542,803 11/1970 Porret et al. ......................... 548/310
3,779,949 12/1973 Porret et al. ......................... 548/310
4,105,774 8/1978 Driscoll et al. ..................... 314/389

Primary Examiner—Robert T. Bond
Attorney, Agent, or Firm—Browdy anbd Neimark

[57] ABSTRACT

Several analogues of hexamethylene bis[acetamide] were found to be effective differentiating agents. The most effective of these compounds was 3,3'-(1,6-hexandiyl)bis[5,5-dimethyl-2,4-imidazolinedione].

4 Claims, No Drawings

CHEMICAL DIFFERENTIATING AGENTS

FIELD OF THE INVENTION

The present invention relates to cancer chemotherapy and, more particularly, to compounds which are active differentiating agents.

BACKGROUND OF THE INVENTION

Compounds that induce cancer cells to differentiate to a less malignant phenotype provide an attractive area for the development of new anticancer drugs. One would expect differentiating agents to exhibit reduced toxicity relative to conventional chemotherapeutic agents, since the mechanism of antitumor action of differentiating agents is not based primarily on cytotoxicity.

There are presently a number of compounds which are known to influence cell differentiation and growth characteristics. These materials, which include simple organic molecules as well as proteins, are thought to influence gene expression.

A number of cell lines have been found to differentiate in the presence of small molecules. It was originally discovered that a virus-induced murine erythroleukemia cell line (MELC), when treated with dimethyl sulfoxide, expressed many of the features common to terminally differentiated erythroid cells. Another important in vitro differentiation system is the human HL-60 myeloid leukemia cell line. The two cell lines currently in use primarily for evaluating differentiating properties of small molecules are the MELC and the HL-60.

With dimethyl sulfoxide as a lead compound, many organic compounds with varying degrees of effectiveness have been studied as differentiation inducers. Dimethyl formamide (DMF) and N-methylacetamide cause MELC and HL-60 cells to differentiate, but with optimum concentrations of around 150 and 50 mM, respectively, they are not sufficiently potent to be clinically practical if similar concentrations are required in vivo.

Marks et al., in Proc. Natl. Acad. Sci. U.S.A. 1975, 72, 1003–1006; J. Biol. Chem. 1978, 253, 4214–4218; and Biochim. Biophys. Acta 1980, 605, 325–346; reported that placing two amide functions in the same molecule increased compound potency. Both activity and potency are maximized in the polymethylenebis[acetamide] series with five or six methylene groups. More recently, studies with dicarboxylic acid amides (Hozumi et al., Int. J. Cancer 1979, 23, 119–122) and diamine analogues with different acyl groups (Matsuo et al., Acta Haematol. Jpn. 1984, 47, 926–937) have been reported, but none of the compounds tested appeared to be superior to hexamethylene bis(acetamide), HMBA.

HMBA is presently undergoing clinical trials based on differentiation as a mechanism of antitumor action. In vitro studies in the MELC system show that five day exposure to 5 mM HMBA gives optimum results. However, studies with rats and dogs indicate that these conditions might be difficult to maintain in vivo without significant toxicity.

SUMMARY OF THE INVENTION

It is an object of the present invention to overcome the deficiencies in the prior art, such as those indicated above.

It is another object of the invention to provide improvements in the treatment of cancer.

It is still another object of the present invention to provide compounds which have differentiating activity with lower toxicity than previously known compounds for this purpose.

It is a further object of the present invention to provide compounds which have greater differentiating activity than the previously known compounds.

It is yet a further object of the present invention to provide compounds having differentiating activity which can be readily administered orally or intravenously.

The compounds of the present invention comprise three classes of polymethylene bis-functionalized compounds: amides, imides, and hydrazine derivatives. A wide variety of synthetic procedures were required to synthesize the desired compounds.

DETAILED DESCRIPTION OF THE INVENTION

The compounds of the invention have the general formula $R(CH_2)_nR$, wherein n is 5 or 6 and R is an amide, imide or hydrazine group, preferably N-heterocyclic.

The compound which was found to have the most potent differentiating activity was 3,3'-(1,6-hexanediyl)-bis-[5,5-dimethyl-2,4-imidazolinedione]. This compound has the following formula:

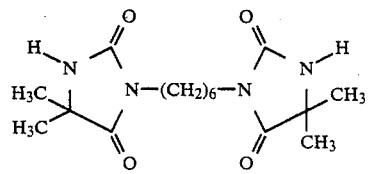

Other compounds which were found to have effective differentiating activity are as follows:

N,N'dimethyl N,N'—hexamethylene bisacetamide $$H_3C-\underset{\underset{O}{\|}}{C}-\underset{\underset{}{|}}{\overset{CH_3}{N}}-(CH_2)_6-\underset{\underset{}{|}}{\overset{CH_3}{N}}-\underset{\underset{O}{\|}}{C}-CH_3$$

1,5-bis(2-oxo-1-piperidinyl)hexane

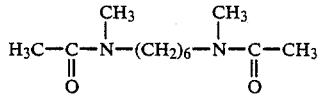

6-(acetylamino)-N—methylhexanamide $$CH_3-\underset{\underset{O}{\|}}{C}-NH-(CH_2)_5-\underset{\underset{O}{\|}}{C}-NHCH_3$$

6-(acetylamino)-N,N'dimethylhexanamide $$CH_3-\underset{\underset{O}{\|}}{C}-NH-(CH_2)_5-\underset{\underset{O}{\|}}{C}-N(CH_3)_2$$

N,N,N,N'tetraacetylhexamethylenediamine

-continued

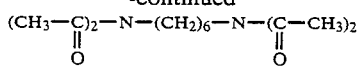

A measurement of the percentage of differentiated cells (%D) is commonly used in the HL-60 system for assessing the relative activities of various compounds. This measurement is most meaningful when the cytotoxicity is low. However, under cytotoxic conditions, a portion of an apparent increase in %D can be the result of an enrichment of the preexisting population of differentiated cells, especially if the cytotoxicity is directed particularly against growing, nondifferentiated cells. This is because %D in the HL-60 system is determined by dividing the number of viable differentiated cells by the number of viable cells. There appears to be no unequivocal method to correct quantitatively for this possible enrichment. However, induction of differentiation in culture would be indicated if there is an increase in the viable-cell concentration as well as a net increase in the concentration of mature cells that is greater than what could have occurred in the control culture at the same cell density. The higher the percent viability (%V), the better the %D value will be as a true measure of differentiation. The lower the %V, the greater will be the possibility that enrichment will influence the results. Therefore, viability determinations are critical for an accurate assessment of inducers of differentiation that are also cytotoxic. There is an inverse nonlinear relationship between the %D and the %V for HMBA. The nature of this relationship indicates that, at lower doses of HMBA, there is relatively more differentiation than cytotoxicity. At higher concentrations of HMBA, the reverse is the case.

It was found that merely N-alkylating the amides did not consistently yield compounds that were universally effective differentiating agents, even though it was found that this process often enhanced effectiveness or potency in the MELC system. Dimethyl-HMBA was slightly more potent and effective than HMBA (cf. Table II), but another analog, diacetylpiperazine was inactive. The 1-piperidone analogue of HMBA was at least as effective as HMBA. The simple compounds piperidone and its N'methyl derivative had been shown previously by Marks et al. op. cit., *Biochim. Biophys. Atca.* to be active but not as effective as HMBA in the MELC system. Other simple cyclic ureas were also known to be effective MELC differentiating agents.

Earlier work by Marks et al., op. cit., *J. Biol. Chem.*, had shown that there was not much difference in differentiation-inducing activity between diamides based on acylated 1,6-diaminohexane (e.g., HMBA) and diamides based on adipic acid. Pentamethylene analogues possessing the molecular characteristics of both compounds in the same molecule were prepared. Both compounds were active, but the N-methyl compound, shown as compound 5 in Table I, proved more effective than the N,N-dimethyl derivative, shown as compound 6 in Table I. N-Methylbutyramide, compound 7 in Table I, which is essentially one-half of an adipic acid diamide, did not induce differentiation. The aromatic benzamide, compound 8 of Table I, was also inactive.

TABLE I

| no. | R | (R(CH$_2$)$_6$R) yield, % | mp, °C. | formula[a] |
|---|---|---|---|---|
| 2 | CH$_3$CON(CH$_3$) | 53 | 138[b] | C$_{12}$H$_{24}$N$_2$O$_2$·0.25H$_2$O[c] |
| 4 | (1-piperidone group) | 41 | 160[b] | C$_{16}$H$_{28}$N$_2$O$_2$·0.5H$_2$O[c] |
| 8 | PhCONH | 64 | 159–160 | C$_{20}$H$_{24}$N$_2$O$_2$ |
| 9 | (CH$_3$CO)$_2$N | 68 | 58 | C$_{14}$H$_{24}$N$_2$O$_4$ |
| 10 | CH$_3$CONHCO | 52 | 180–181 | C$_{12}$H$_{20}$N$_2$O$_4$ |
| 11 | (succinimide group) | 43 | 115 | C$_{14}$H$_{20}$N$_2$O$_4$ |
| 12 | (glutarimide group) | 78 | 102–103 | C$_{16}$H$_{24}$N$_2$O$_4$ |
| 13 | (dimethylhydantoin group) | 42 | 145–146 | C$_{16}$H$_{26}$N$_4$O$_4$ |

TABLE I-continued

| no. | R | (R(CH$_2$)$_6$R) yield, % | mp, °C | formula[a] |
|---|---|---|---|---|
| 14 | H\N—\|—N / Ph—\|—Ph, with C=O groups (phenytoin-acetyl structure) | 74 | 261–263 | C$_{36}$H$_{34}$N$_4$O$_4$ |
| 15 | CH$_3$CONHNHCO | 74 | 242–243 | C$_{12}$H$_{22}$N$_4$O$_4$ |
| 16 | CH$_3$CONHNHCONH | 78 | 204 | C$_{12}$H$_{24}$N$_6$O$_4$ |
| 17 | p-CH$_3$PhSO$_2$NH | 49 | 150–151 | C$_{20}$H$_{28}$N$_2$O$_4$S$_2$[d] |

[a]Correct C, H, N analyses (±0.4% of theory).
[b]Bp (°C. at 0.1 torr).
[c]Correct analysis also for oxygen.
[d]Correct analysis also for sulfur.

Several bis-imides were prepared to determine whether this group could replace the HMBA amide function. The cyclic succinimide, compound 11 in Table I, and the glutarimide, compound 12 in Table I, analogues were inactive, but the acyclic N,N'-diacetyl-HMBA, compound 9 in Table I, was superior to the parent compound in terms of both potency and effectiveness. Incorporation of hydantoin groups in place of the amides produced an active compound in the case of the 5,5-dimethyl analogue, compound 13 in Table I. This compound is almost ten times more potent than HMBA. The phenytoin analogue, compound 14 in Table I, is very insoluble, and this property may have limited its activity. However, compound 14 could be effective when administered orally in vivo.

In limited studies with hydrazine containing molecules, the acetyl hydrazide, compound 15, and semicarbazide, compound 16, of Table I, were ineffective. The bis-tosyl derivative of hexamethylenediamine, compound 17 of Table I, was also not effective.

While a differentiating agent without cytotoxicity would be ideal, it is conceivable that an agent possessing both differentiating and cytotoxic properties might be useful if some selective cytotoxicity were observed for tumor cells. For this reason, compounds 3–6 and 8–17 were evaluated in vivo against murine intraperitoneal P388 leukemia under the standard National Cancer Institute Protocol. In general, neither significant toxicity nor antitumor activity was observed at doses of 50–400 mg/kg with a day 1–5 treatment schedule.

Among the compounds evaluated in the present series, the hexamethylene bis-amide family shows effectiveness, with several analogues, compounds 2, 4, and 5, possessing differentiating activity similar to that of HMBA. Diacetyl-HMBA, compound 9, is slightly more potent and somewhat more effective than HMBA. While none of these compounds appears to have an advantage over HMBA based on a greater differentiation inducing activity to toxicity ratio, compound 13 is about 10 times more potent than HMBA with approximately equivalent differentiating properties. Differentiation studies were conducted as previously described by Breitman et al., *Methods for Serum-free Culture for Neuronal and Lymphoid Cells*, A. R. Liss, New York, 1984, Chapter 15. The studies were conducted with the HL-60 human myeloid leukemia cell line. In this study, minimal compound activity is defined as a %D value of 20% or greater. While all compounds synthesized were evaluated, only those meeting this minimum criterion are described in Table II. Differentiation was assessed by counting the cells that reduced nitro blue tetrazolium (NBT) to its black formazan form. This reaction is dependent on the production of superoxide anion as a reducing agent, and is characteristic of differentiated but not undifferentiated HL-60 cells. Formazan production is also dependent on cell viability, since only living cells are capable of superoxide production. Total cell numbers were counted with a Coulter counter, and the total percentage of the total cells that were viable was determined by trypan blue exclusion. The initial cell concentration was 2×10$^5$/mL, and cells were counted on day four. Test compounds were generally insoluble in water and were dissolved in ethanol or dimethyl sulfoxide prior to addition to the cell suspension. Final concentrations of dimethyl sulfoxide in the test system did not exceed 77 mM. This concentration had no effect on cell differentiation, as can be seen in Table II.

TABLE II

| compd | concn, mM | total cells (10$^{-5}$/mL) | % D[a] | % V[b] |
|---|---|---|---|---|
| control | | 12.0 ± 3.9 (18)[c] | 4 | 96 |
| 1(HMBA) | 2.0 | 6.9 ± 0.35 (2) | 32 | 74 |
| | 3.0 | 5.2 ± 1.40 (11) | 59 | 68 |
| | 4.0 | 3.9 ± 0.62 (5) | 84 | 29 |
| Me$_2$SO | 38 | 9.7 (1) | 6 | 97 |
| | 64 | 9.8 ± 1.1 (2) | 9 | 96 |
| | 77 | 9.3 (1) | 6 | 94 |
| 2 | 1.0 | 11.2 (1) | 10 | 90 |
| | 2.0 | 7.0 (1) | 74 | 57 |
| | 2.5 | 5.1 (1) | 93 | 32 |
| | 3.0 | 4.2 (2) | 94 | 30 |
| 4 | 1.0 | 8.3 (1) | 12 | 87 |
| | 2.0 | 7.6 (1) | 40 | 65 |
| | 2.5 | 6.8 (1) | 72 | 62 |
| | 3.0 | 3.7 (1) | 87 | 25 |
| 5 | 3.0 | 6.8 ± 0.48 (2) | 40 | 72 |
| | 4.0 | 6.9 ± 0.26 (2) | 71 | 56 |
| 6 | 1.0 | 7.0 ± 3.2 (2) | 24 | 85 |
| | 1.5 | 10.7 (1) | 13 | 78 |
| | 2.0 | 9.4 (1) | 12 | 82 |
| 9 | 2.0 | 5.3 ± 2.2 (2) | 65 | 71 |
| | 2.5 | 4.8 (1) | 76 | 51 |
| | 3.0 | 3.0 ± 0.65 (3) | 80 | 45 |
| 13 | 0.1 | 8.7 ± 2.9 (2) | 9 | 96 |
| | 0.3 | 4.8 ± 1.4 (4) | 26 | 82 |
| | 0.4 | 4.2 ± 1.35 (2) | 45 | 53 |
| | 0.5 | 3.1 ± 0.92 (2) | 76 | 43 |

[a]Percent differentiation; average value for multiple experiments.
[b]Percent viability; average value for multiple experiments.
[c]Number of experiments in parentheses.

Commercially available reagents were purchased from Aldrich Chemical Co. Compound 3 was obtained from the Drug Synthesis and Chemistry Branch, National Cancer Institute.

Thomas-Hoover melting points and Kugelrohr boiling points are uncorrected.

$^1$H NMR data (CDCl$_3$) were obtained for each compound an a Varian T-60 instrument. Since the spectra of most compounds had many similarities, individual data are not presented. The absorptions of internal methylene, acyl methyl, nitrogen-attached methyl, and nitrogen-attached methylene groups generally appeared at about 1.4 (broad), 2.0 (singlet), 2.9 (doublet), and 3.2 (broad multiplet), respectively, relative to tetramethylsilane. The electron-impact mass spectrum of compound 7 was obtained with a VG Analytical 7070E mass spectrometer.

EXAMPLE I 3,3'-(1,6-hexanediyl)bis[5,5-dimethyl]-2,4-imidazoline

To a solution of 5,5-dimethylhydantoin in absolute ethanol was added an equimolar amount of potassium hydroxide. The mixture was stirred until a homogenous solution was obtained. Then, 0.25 molar equivalent of 1,6-dibromohexamne was added in one portion, and the mixture was refluxed for twenty hours. Three volumes of water was added, and the aqueous phase was extracted with chloroform. The organic layer was washed with water and dried over magnesium sulfate, and the solvent was removed in vacuo to obtain pure product.

EXAMPLE II

N,N'-dimethyl-N,N'-hexamethylenebis[acetamide]

To a 50% oil suspension of sodium hydride (3.36 grams, 70 mmol) in dry THF (60 mL) under nitrogen was added N-methylacetamide (5.0 grams, 69 mmol) in 10 mL THF, and the mixture was refluxed for five hours. Then, 6.0 grams (24 mmol) of 1,6-dibromohexane was added, and the resulting mixture was refluxed for an additional two hours. Two hundred milliliters of cold water was added, and the aqueous phase was extracted with 100 mL of chloroform three times. The organic layer was washed with water and dried over magnesium sulfate, and the solvent was evaporated in vacuo to yield an oil. Kugelrohr distillation of this material gave 2.5 grams of a pure oil (53%), boiling point 138° C. (0.1 torr).

EXAMPLE III 1,5-bis(2-oxo-1-piperidinyl)hexane

To a 50% oil suspension of sodium hydride (3.16 grams, 65 mmol) in 60 mL dry DMF under nitrogen was added 6.53 grams (65 mmol) of delta-valerolactam. The mixture was stirred overnight. Then, 4.0 grams (16.3 mmol) of 1,6-dibromohexane was added, and the mixture was stirred for an additional six hours. Two hundred mL of water was added, and the aqueous phase was extracted with chloroform. The organic layer was washed with water and dried over magnesium sulfate, and the solvent was removed in vacuo. Fractional distillation afforded 1.9 gram (41%) of pure material as an oil, boiling point 160° C. (0.1 torr).

EXAMPLE IV 6-(acetylamino)-N-methylhexanamide

Methyl 6-acetamidohexanoate was prepared as a low-melting solid by sequential treatment of 6-acetamido hexanoic acid with thionyl chloride and methanol. Five grams of this compound, (27 mmol) was dissolved in an excess of 40% aqueous methylamine solution, and the resulting mixture was stirred for sixteen hours at room temperature. The reaction mixture was saturated with sodium chloride and extracted several times with chloroform. The organic layer was dried over magnesium sulfate, and the solvent was removed in vauo to yield a crude residue. Recrystallization from THF yielded 4.5 grams (90%) of pure product, melting point 99°–100° C.

EXAMPLE V 6-(acetylamino)-N,N-dimethylexanamide

This compound was prepared as described in Example V. The compound was obtained in 76% yield as an oil of boiling point 168° C. (2 torr).

EXAMPLE VI

N,N,N',N'-tetraacetylhexamethylenediamine

This compound was prepared by the general procedure of Mariella and Brown, as reported in *J. Org. Chem.* 1971, 36, 735–737. A mixture of 7.0 grams (35 mmol) hexamethylenebisacetamide, 4.0 grams (48 mmol) anhydrous sodium acetate, and 80 mL acetic anhydride was refluxed for twenty hours. Excess acetic anhydride was removed in vacuo, and 60 mL water was added to the residue. The aqueous phase was extracted with 100 mL chloroform three times. The organic layer was washed with water, dried over magnesium sulfate, and passed through a short silica gel column (CHCl$_3$). After solvent removal 6.8 grams (68%) of pure compound was isolated.

The compounds of the present invention are administered in the treatment of cancer at doses ranging from 10–1000 mg/Kg per day. The compounds can be administered in a variety of methods, including orally, intravenously, and the like, using pharmaceutically acceptable carriers.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for causing malignant cells to differentiate to a less malignant phenotype comprising treating said malignant cells with an effective amount of a pharmaceutical composition comprising an effective amount of 3,3'-(1,6-hexanediyl)bis([5,5-dimethyl-2,4-imidazolinedione] in a pharmaceutical acceptable carrier.

2. The method according to claim 1 wherein the imidazolinedione is administered at doses ranging from 10 to 1000 mg/kg of body weight of the patient per day.

3. The method according to claim 1 wherein the composition is administered orally.

4. The method according to claim 1 wherein the composition is administered intravenously.

* * * * *